US00PP36018P2

(12) United States Plant Patent
Hattori

(10) Patent No.: US PP36,018 P2
(45) Date of Patent: Jul. 16, 2024

(54) ***HELLEBORUS* PLANT NAMED 'PIKE'S PEAK'**

(50) Latin Name: ***Helleborus* x *sternii* X *Helleborus argutifolius***
Varietal Denomination: Pike's Peak

(71) Applicant: Miyoko Hattori, Tokyo (JP)

(72) Inventor: Miyoko Hattori, Tokyo (JP)

( * ) Notice: Subject to any disclaimer, the term of this patent is extended or adjusted under 35 U.S.C. 154(b) by 0 days.

(21) Appl. No.: 18/235,835

(22) Filed: Aug. 19, 2023

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. Anne Whealy

(57) ABSTRACT

A new and distinct cultivar of *Helleborus* plant named 'Pike's Peak', characterized by its upright to outwardly spreading and mounding plant habit; moderately vigorous to vigorous growth habit; silvery grey-colored leaflets with distinctive green-colored venation; freely flowering habit; light green-colored flowers that are held level with the foliar plane; and good garden performance.

2 Drawing Sheets

Figure 1:
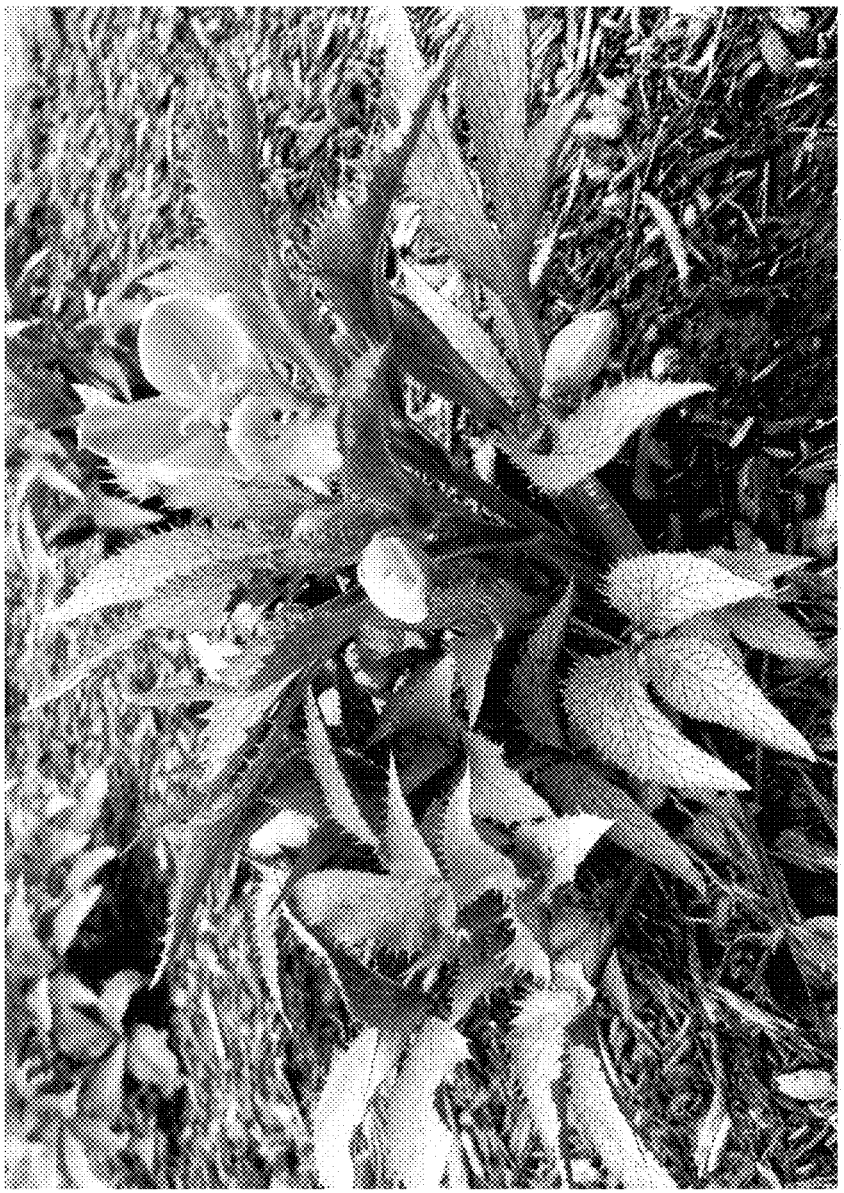

Botanical designation: *Helleborus* x *sternii* X *Helleborus argutifolius.*

Cultivar denomination: 'PIKE'S PEAK'.

BACKGROUND OF THE INVENTION

The present invention relates to a new and distinct cultivar of *Helleborus* plant, botanically known as *Helleborus* x *sternii* X *Helleborus argutifolius* and hereinafter referred to by the name 'Pike's Peak'.

The new *Helleborus* plant is a product of a planned breeding program conducted by the Inventor in Tokyo, Japan. The objective of the breeding program was to create new vigorous and freely-flowering *Helleborus* plants with silvery leaflets with serrate margins and attractive flowers.

The new *Helleborus* plant originated from a cross-pollination conducted by the Inventor in Toyko, Japan in March, 2016 of a proprietary selection of *Helleborus* x *sternii* identified as code "A", as the female, or seed, parent, not patented, with a proprietary selection of *Helleborus argutifolius* identified as code "B" as the male, or pollen, parent, not patented. The new *Helleborus* plant was discovered and selected by the Inventor as a single flowering plant from within the progeny of the stated cross-pollination grown in a controlled greenhouse environment in Tokyo, Japan in March, 2018.

Asexual reproduction of the new *Helleborus* plant by divisions in a controlled greenhouse environment in Tokyo, Japan since March, 2018, has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype of the new *Helleborus* plant may vary somewhat with variations in environmental conditions such as temperature and light intensity without, however, any variance in genotype of the new *Helleborus* plant.

The following traits have been repeatedly observed and are determined to be the unique characteristics of 'Pike's Peak'. These characteristics in combination distinguish 'Pike's Peak' as a new and distinct *Helleborus* plant:

1. Upright to outwardly spreading and mounding plant habit.
2. Moderately vigorous to vigorous growth habit.
3. Silvery grey-colored leaflets with distinctive green-colored venation.
4. Freely flowering habit.
5. Light green-colored flowers that are held level with the foliar plane.
6. Good garden performance.

Plants of the new *Helleborus* differ primarily from plants of the female parent selection in the following characteristics:

1. Plants of the new *Helleborus* are more mounding than plants of the female parent selection.
2. Leaves of plants of the new *Helleborus* are more serrate than leaves of plants of the female parent selection.

Plants of the new *Helleborus* and the male parent selection differ primarily from plants of the male parent selection in leaf coloration as leaves of plants of the new *Helleborus* have more distinct venation than leaves of plants of the male parent selection.

Plants of the new *Helleborus* can be compared to plants of *Helleborus niger* X *Helleborus* x *sternii* 'COSEH 860', disclosed in U.S. Plant Pat. No. 23,773. In side-by-side comparisons, plants of the new *Helleborus* differ from plants of 'COSEH 860' in the following characteristics:

1. Leaflets of plants of the new *Helleborus* are silvery grey-colored leaflets with distinctive green-colored venation whereas leaflets of plants of 'COSEH 860' are dark greyed green in color.
2. Plants of the new *Helleborus* are not as freely flowering as plants of 'COSEH 860'.

3. Flowers of plants of the new *Helleborus* are light green in color whereas flowers of plants of 'COSEH 860' are light yellow green in color.
4. Plants of the new *Helleborus* have shorter peduncles than plants of 'COSEH 860'.
5. Flowers of plants of the new *Helleborus* have fewer stamens than plants of 'COSEH 860'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'Pike's Peak' grown in an outdoor nursery.

Figure 2:
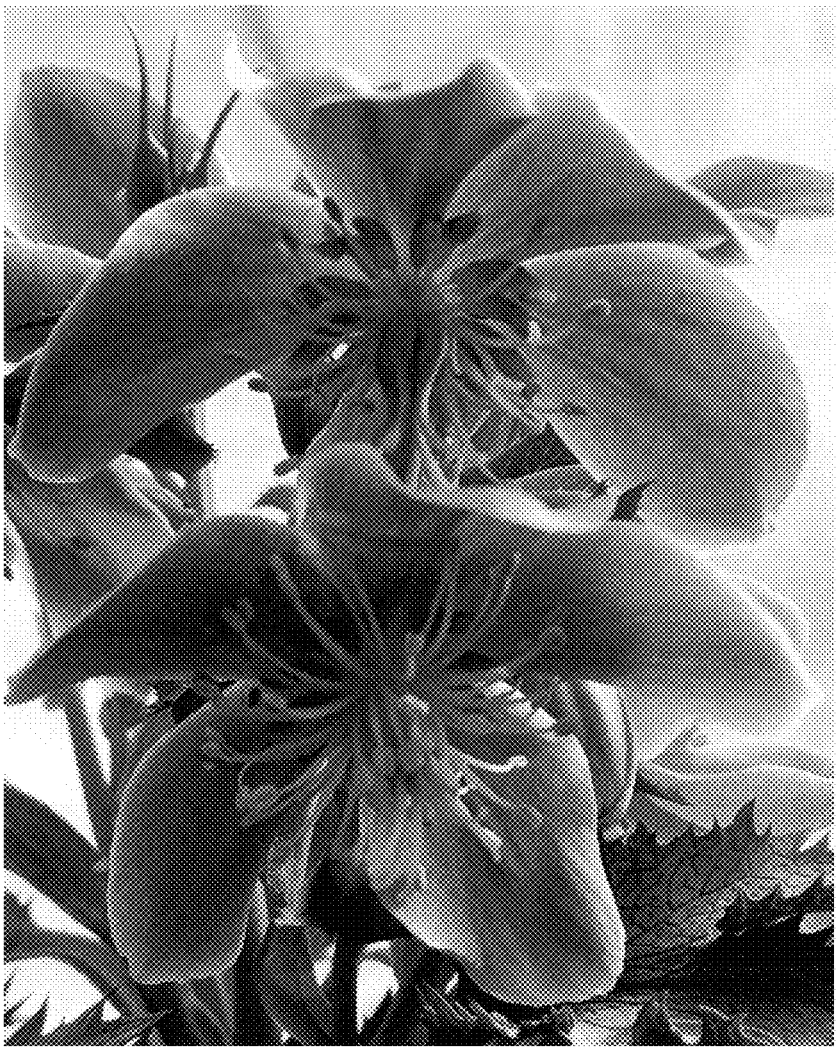

The photograph on the second sheet (FIG. 2) is a close-up view of typical flowers of 'Pike's Peak'.

DETAILED BOTANICAL DESCRIPTION

The aforementioned photographs and following observations, measurements and values describe plants grown during the early spring in an outdoor nursery in Smoketown, Pennsylvania and under cultural practices typical of commercial *Helleborus* production. During the production of the plants, day temperatures ranged from 18 C to 22 C, night temperatures ranged from 5 C to 10 C and light levels ranged from 30 to 70 Klux. Plants were 1.75 years old when the photograph and the description were taken. In the following description, color references are made to The Royal Horticultural Society Colour Chart, Sixth Edition, except where general terms of ordinary dictionary significance are used.

Botanical classification: *Helleborus* x *sternii* X *Helleborus argutifolius* 'Pike's Peak'.

Parentage:

*Female, or seed, parent.*—*Helleborus* x *sternii* identified as code "A", not patented.

*Male, or pollen, parent.*—Proprietary selection of *Helleborus argutifolius* identified as code "B", not patented.

Propagation:

*Type.*—By meristem culture.

*Time to initiate roots.*—About three to four weeks at soil temperatures about 21 C to 22 C.

*Time to produce a rooted young plant.*—About six to eight weeks at soil temperatures about 21 C to 22 C.

*Root description.*—Fleshy, medium in thickness; typically brown to white in color, actual color of the roots is dependent on substrate composition, water quality, fertilizer type and formulation, substrate temperature and physiological age of roots.

*Rooting habit.*—Moderate branching; medium density.

Plant description:

*Plant and growth habit.*—Herbaceous perennial; upright to outwardly spreading and mounding plant habit; moderately vigorous to vigorous growth habit and moderate growth rate; leaves arranged in basal rosettes.

*Plant height, soil level to top of foliar plane.*—About 24 cm.

*Plant height, soil level to top of floral plane.*—About 24 cm.

*Plant diameter* (*area of spread*).—About 40 cm.

Leaf description:

*Arrangement.*—Leaves arranged alternately in a basal rosette; leaves palmately compound with typically three leaflets per leaf. Leaflet length: About 10 cm to 14 cm.

*Leaflet width.*—About 2 cm to 3 cm.

*Leaflet shape.*—Narrowly elliptic.

*Leaflet apex.*—Acute.

*Leaflet base.*—Attenuate to oblique.

*Leaflet margin.*—Serrate.

*Leaflet texture and luster, upper and lower surfaces.*—Smooth, glabrous; leathery; matte.

*Leaflet venation pattern.*—Pinnate and reticulate.

*Leaflet color.*—Developing leaflets, upper surface: Close to 190A to 190B. Developing leaflets, lower surface: Close to 194B to 194C mottled with close to N77A. Fully expanded leaflets, upper surface: Close to 188C; midvein, close to N144A to N144B and at the petiole, close to 138A. Fully expanded leaflets, lower surface: Close to 187B to 187C overlain with close to 190B; venation, close to 187B to 187C and at the petiole, close to 187A.

*Petioles.*—Length, fully expanded leaflets: About 5 cm to 7 cm. Diameter, fully expanded leaflets: About 1 mm to 4 mm. Strength: Strong. Texture and luster, upper and lower surfaces: Smooth, glabrous; waxy; matte. Color: Developing leaflets, upper surface: Close to 59B; at the center and speckles overall, close to N148D. Developing leaflets, lower surface: Close to 59B; at the apex and speckles overall, close to N148D. Fully expanded leaflets, upper surface: Close to 145B with speckles, close to 59A. Fully expanded leaflets, lower surface: Close to 145C to 145D with speckles, close to 59A.

Flower description:

*Flower shape and habit.*—Single rotate cyanthiform flowers arranged in terminal and axillary cymes; freely flowering habit with typically about 20 to 30 flowers developing per plant; flowers face outwardly to upright.

*Fragrance.*—None detected.

*Natural flowering season.*—Plants flower in April and May in Pennsylvania.

*Flower longevity on the plant.*—About three weeks; sepals are persistent and other flower parts are not persistent.

*Flower buds.*—Length: About 1.5 cm to 2 cm. Diameter: About 1 cm to 1.5 cm. Shape: Ovoid. Texture and luster: Smooth, glabrous; matte. Color: Close to 145B.

*Inflorescence height.*—About 24 cm.

*Inflorescence diameter.*—About 14 cm to 20 cm.

*Flower diameter.*—About 4 cm to 5 cm.

*Flower depth* (*height*).—About 1 cm.

*Petals.*—None observed; transformed into nectaries.

*Sepals.*—Quantity and arrangement: About five or six arranged in a single whorl. Length: About 2.3 cm. Width: About 1.2 cm to 1.8 cm. Shape: Oval. Apex: Obtuse. Base: Acute. Margin: Finely serrate. Texture and luster, upper and lower surfaces: Smooth, glabrous; matte. Color: When opening, upper surface: Close to 146B and towards the margins, close to 145C. When opening, lower surface: Close to 145C. Fully opened, upper surface: Close to 146C and towards the margins, close to 1C to 1D. Fully opened, lower surface: Close to 148C and towards the margins, close to 145C.

*Flower bracts*.—Quantity and arrangement: About one or two at the base of the flower. Length: About 7 cm to 11 cm. Width: About 2 cm to 3 cm. Shape: Narrowly elliptic. Apex: Acute. Base: Attenuate. Margin: Serrate. Texture and luster, upper and lower surfaces: Smooth, glaucous; matte. Color: When opening, upper surface: Close to 191A to 191B; midvein, close to N144C and at the base, close to 59A. When opening, lower surface: Close to 147C slightly mottled with close to 59A. Fully opened, upper surface: Close to 190A to 190B; venation, close to N144C. Fully opened, lower surface: Close to 194B to 194C mottled with close to N77A; venation, close to N144C and at the base, close to 60A.

*Peduncles*.—Length: About 5 cm to 6 cm. Diameter: About 3 mm by 5 mm. Strength: Moderately strong to strong; flexible. Aspect: About 35 to 40 degrees from plant axis. Texture and luster: Smooth, glabrous; somewhat glossy. Color: Close to 145B with speckles, close to 59A to 59B.

*Reproductive organs*.—Stamens: Quantity per flower: About 50. Filament length: About 1 cm. Filament color: Close to 3C. Anther shape: Oblong. Anther size: About 1 mm by 2 mm. Anther color: Close to 3A. Pollen amount: None observed. Pistils: Quantity per flower: About seven to nine. Pistil length: About 1.2 cm to 1.3 cm. Stigma shape: Tapered, pointed. Stigma color: Close to 60A. Style length: About 1 cm to 1.2 cm. Style color: Close to 150B to 150C. Ovary color: Close to 150C. Nectaries: Quantity per flower: About 13 to 15. Length: About 8 mm to 9 mm. Width: Close to 1 mm to 2 mm. Shape: Tubular. Apex: Rounded. Margin: Entire; ruffled at apex; slightly undulate. Texture and luster: Smooth, glaucous; matte to slightly glossy. Color: Close to N144C and towards the apex, close to N144B. Seeds and fruits: To date, seed and fruit development have not been observed on plants of the new *Helleborus*.

Garden performance: Plants of the new *Helleborus* have been observed to have good garden performance and to tolerate rain, wind and temperatures ranging from about −15 C to about 34 C.

Pathogen & pest resistance: To date, plants of the new *Helleborus* have not been observed to be resistant to pathogens and pests common to *Helleborus* plants.

It is claimed:

1. A new and distinct *Helleborus* plant named 'Pike's Peak' as illustrated and described.

* * * * *